US009572545B2

(12) United States Patent
Chen et al.

(10) Patent No.: US 9,572,545 B2
(45) Date of Patent: Feb. 21, 2017

(54) RADIOTHERAPY SYSTEM ADAPTED TO MONITOR A TARGET LOCATION IN REAL TIME

(75) Inventors: Yu-Jen Chen, Taipei (TW); Chia-Yuan Liu, Taipei (TW); Wen-Chung Chang, Taipei (TW); Chin-Sheng Chen, Taipei (TW)

(73) Assignees: Mackay Memorial Hospital, Taipei (TW); National Taipei University of Technology, Taipei (TW)

( * ) Notice: Subject to any disclaimer, the term of this patent is extended or adjusted under 35 U.S.C. 154(b) by 814 days.

(21) Appl. No.: 13/466,142

(22) Filed: May 8, 2012

(65) Prior Publication Data

US 2013/0085387 A1    Apr. 4, 2013

(30) Foreign Application Priority Data

Sep. 30, 2011    (TW) .............................. 100135708 A

(51) Int. Cl.
*A61B 8/08*    (2006.01)
*A61B 8/00*    (2006.01)
*A61N 5/10*    (2006.01)

(52) U.S. Cl.
CPC ............. *A61B 8/085* (2013.01); *A61B 8/4218* (2013.01); *A61B 8/4263* (2013.01); *A61B 8/523* (2013.01); *A61B 8/5261* (2013.01); *A61B 8/565* (2013.01); *A61B 8/587* (2013.01); *A61N 5/1037* (2013.01); *A61N 5/1067* (2013.01); *A61N 2005/1058* (2013.01); *G06T 2207/10081* (2013.01);

(Continued)

(58) Field of Classification Search
CPC ... A61B 6/4417; A61B 6/4458; A61B 6/4476; A61B 8/4218; A61B 19/5244; A61N 2005/1058; A61N 2005/1059; A61N 5/1064; A61N 5/1067
See application file for complete search history.

(56) References Cited

U.S. PATENT DOCUMENTS 5,090,002 A *    2/1992    Chow et al. ............... 369/44.28
6,675,040 B1 *    1/2004    Cosman ....................... 600/427
(Continued)

OTHER PUBLICATIONS

Schlosser et al., "Telerobotic system concept for real-time soft-tissue imaging during radiotherapy beam delivery," Nov. 22, 2010, Med. Phys., vol. 37 (12), pp. 6357-6367.*

(Continued)

*Primary Examiner* — Tse Chen
*Assistant Examiner* — Nate S Sunwoo
(74) *Attorney, Agent, or Firm* — Lin & Associates Intellectual Property, Inc.

(57) ABSTRACT

The present invention provides a radiotherapy system that can monitor a target location in real time. The radiotherapy system includes a remote control system operable to actuate a real-time image capturing device to acquire images in real time for monitoring the target location. The system also includes an image registration system that can register the acquired image with an image previously captured for the treatment plan, whereby it can be determined whether the patient's tumor is in the beam's eye view of the treatment plan. By confirming that the tumor is in the range of the beam's eye view, the accuracy of the treatment can be improved, and the irradiated area can be reduced, which makes the radiation treatment safer.

19 Claims, 8 Drawing Sheets

(52) U.S. Cl.
CPC .............. *G06T 2207/10132* (2013.01); *G06T 2207/30056* (2013.01)

(56) References Cited

U.S. PATENT DOCUMENTS

| | | | |
|---|---|---|---|
| 2006/0213287 A1* | 9/2006 | Sakano | 73/862.042 |
| 2007/0038058 A1* | 2/2007 | West | A61N 5/1049 600/407 |
| 2008/0143718 A1* | 6/2008 | Ray et al. | 345/424 |
| 2009/0003528 A1* | 1/2009 | Ramraj et al. | 378/119 |

OTHER PUBLICATIONS

Danlu, "Robotic Arm Mimics Human Movement," Feb. 17, 2011, Xinhuanet, <http://news.xinhuanet.com/english2010/video/2011-02/17/c_13736448.htm>.*

Purdy, "3D Treatment Planning and Intensity Modulated Radiation Therapy," Oct. 1, 1999, Oncology, p. 2.*

Koizumi et al., "Continuous Path Controller for the Remote Ultrasound Diagnostic System," Apr. 15, 2008, IEEE/ASME Transactions on Mechatronics, vol. 13, No. 2, pp. 206-218.*

Y. Chen et al., "Integration of Multidisciplinary Technologies for Remote-Controlled, Dynamic Tracking, and Real-Time Target Verification for Conformal Radiotherapy: a Prototype of Target Visualization System", 53rd Annual meeting in Miami Beach, FL, Oct. 2-6, 2011.

Yu-Lin Liu, "Edge Based Image Registration between Ultrasonography and Similarity Transformed CT images", Thesis, Jul. 2011.

Sheng-Fu Hsu, "Hybrid Force and Vision-Based Tracking Control of a Six-DOF Robotic Manipulator", Thesis, Aug. 2011.

Sheng-Ren Yang, "Image Registration Between Ultrasonography and CT images Based on GPU and CPU Cooperated Architecture", Thesis, Jul. 2011.

* cited by examiner

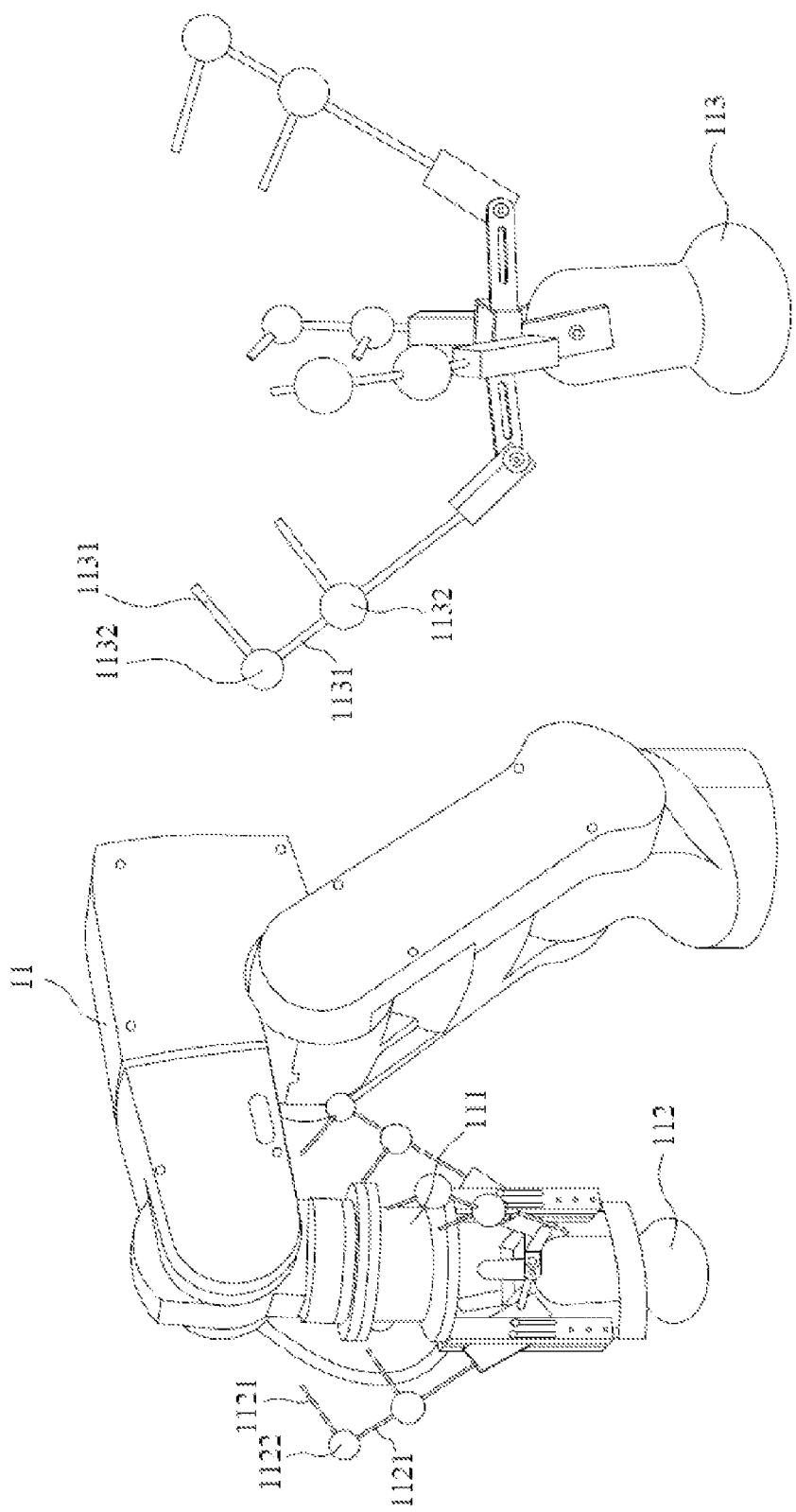

RADIOTHERAPY SYSTEM ADAPTED TO MONITOR A TARGET LOCATION IN REAL TIME

BACKGROUND OF THE INVENTION

1. Field of the Invention

The present invention relates to radiotherapy systems, and more particularly to a radiotherapy system that can monitor a target location in real time.

2. The Prior Arts

In medical science, cancer is also called malignant neoplasm, which is a disorder in the mechanism that controls the growth of cells. Cancer has become a major cause of death in developed countries. In Taiwan, the statistics show that cancer has been the first cause of mortality for 29 years. There are multiple types of cancers, and the seriousness of the cancers depends on several factors including the location of the cancer cells, the degree of malignant growth, and the occurrence of distant metastasis. Many cancers can be treated and even cured, depending on its type, location and development stage. With respect to patients who are in locally-advanced cancers which cannot be removed by surgery ablation or who want to preserve the affected organ, radiotherapy may be an effective treatment.

Radiotherapy uses radiation to kill the cancer cells or reduce the size of the tumor cells. Radiotherapy includes external beam radiotherapy (or teletherapy) and brachytherapy. Because the cancer cells grow faster than normal cells, the application of radiation can destroy the genetic material of the cells, which can stop the growth or replication of the cells. The growth of the cancer cells thus can be restrained. However, the effect of radiotherapy is only limited to the region that receives the radiation. The goal of radiotherapy is to kill a maximum amount of cancer cells without affecting the healthy tissue. Radiotherapy may be adapted for treating solid tumor at diverse locations, such as brain, breast, uterine cervix, throat, lung, kidney, prostate, skin, stomach, uterus, or soft tissue. In certain situations, radiotherapy may also be used to treat leukemia and lymphoma. Whether the tumor and side effects are effectively controlled is based on the proper radiation dose that is applied to kill the tumor cells without significantly damaging the surrounding healthy cells.

As technology advances, the development of new imaging equipment and radiotherapy apparatuses makes possible conformal radiotherapy. Three-dimensional conformal radiotherapy uses high-energy X rays that are emitted in different fields and under different angles, so that the dose can be accumulated in space. The region of high dosage can be thereby distributed conformal to the shape of the tumor, and a mask can protect the healthy tissue surrounding the tumor. With this treatment method, the tumor receives a concentrated dosage, whereas the dosage received by the healthy tissue and important organs can be reduced. As a result, the local control rate is increased, and the occurrence of complications is reduced.

The radiation sources most frequently implemented in radiotherapy are linear accelerators that can generate curative high-energy electron or X rays that can be adjustable. A multi-leaf collimator may also be used to control the direction and shape of the radiation beam to conform with the shape of the tumor to treat. Alternatively, the radiotherapy can also use a cyclotron to generate high-energy protons for treating the tumor. Recently, several conformal radiotherapy approaches have been developed, for example intensity modulated radiotherapy and tomotherapy, which have been clinically tested as applicable methods.

Usually, there may be several weeks between the time when computed tomography images are taken from the patient for evaluating the treatment plan, and the time when radiation treatment is actually applied. Whether the shape of the tumor has changed in this time interval may be verified by test slices shot under different angles before the treatment, whereby the exactitude of the angle and field of the treatment can be confirmed. However, inadvertent displacements of the target region may happen during the treatment. These displacements may be caused by, for example, breathing movements or movements of the patient owing to discomfort or prolonged holding of a same position. If it is small, the displacement may be unperceived by the operator. As a result, the region where radiation is actually applied may be offset from the initial target, so that the tumor does not receive the prescribed radiation dose, whereas the surrounding healthy tissue may be damaged by an exposure to excessive radiation. While conformal radiotherapy has been widely accepted for treating cancer tumors, the accuracy of this method mainly relies on the computed tomography images that are usually generated in the beam's eye view. The pretreatment verification mentioned previously is also based on the same computed tomography images that are not shot in real time. Given these limitations, current radiotherapy techniques cannot ensure that the treated target is continuously in the range of the radiation beam.

SUMMARY OF THE INVENTION

An aspect of the present invention is to provide a radiotherapy system that can solve the problems of the prior art, and can monitor in real time a target location. The radiotherapy system comprises a radiation source; a real-time image capturing device mounted with a robotic manipulator, wherein while radiation is emitted from the radiation source, the real-time image capturing device captures an image of a targeted location in real time; a remote actuating system comprised of the robotic manipulator and a visual servoing and force control system, wherein the robotic manipulator has multiple degrees of freedom and is equipped with a six-axis force sensor, the robotic manipulator being controlled by the visual servoing and force control system or other position servo controls to actuate the real-time image capturing device; and an image registration system operable to register in real time an image obtained from the real-time image capturing device with a pre-stored image. While radiation treatment is conducted, the real-time image capturing device is freely movable on different regions of a patient's body to generate a monitor image, the remote actuating system controlling a position of the real-time image capturing device, such that the real-time image capturing device is placed at the targeted location, and is kept in position with a desirable contact force on the targeted location of the patient's body.

In one embodiment of the present invention, the real-time image capturing device is an ultrasound probe or an image monitoring device held by the robotic manipulator. The radiation source comprises a linear accelerator, a cyclotron, or a synchronous accelerator. The visual servoing and force control system is operable to actuate the robotic manipulator to track and control the position, orientation and contact force of the real-time image capturing device. The pre-stored image is a computed tomography image, a positron emission tomography-computed tomography image, or a nuclear magnetic resonance image. The image registration system is operable to perform image segmentation, image slice interpolation and slice reconstruction, feature extraction, and image registration. The ultrasound probe is an external 2D probe, an internal probe, a mechanical 3D probe, a freehand 3D probe, a matrix 3D probe, or a real-time 4D probe. The ultrasound probe applies real-time gray scale imaging, color and power Doppler imaging, harmonic sonography, sonographic elastography, or contrast enhancement ultrasonography. The other position servo systems comprise magnetic or electronic position servo systems. The image registration system registers a first image obtained from the real-time image capturing device and not in a beam direction with a pre-stored image, so that the first image is converted into an image of the treated target in the beam's eye view. Therefore, during radiation treatment, the radiotherapy system can monitor in real time whether the tumor is covered by the beam's eye view.

By integrating the real-time capturing device, the visual servoing and force control system and the image registration system, the radiotherapy equipment can determine in real time whether the position of the irradiated target (for example a tumor) is covered by the beam's eye view of each radiation angle. Accordingly, the irradiation parameters can be modified any time, which can improve the uncertainty of clinical treatment of tumors by radiation. Because the present invention can accurately monitor the position of the tumor, the tolerance area set around the tumor in the treatment plan to compensate for inadvertent displacement can be reduced, which can reduce damages to the normal tissue that surrounds the tumor. With the ability to determine that the tumor is within the range of the beam's eye view preset in the treatment plan, the treatment can be more accurate, and the area subjected to irradiation can be reduced, which makes the treatment safer.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 2A is a schematic view showing the placement of color balls of different colors and black rods with the ultrasound probe;

FIG. 2B is a schematic view showing the placement of color balls and black rods with the handheld probe;

DETAILED DESCRIPTION OF THE PREFERRED EMBODIMENTS

Embodiments of the present invention use ultrasound images to accurately monitor in real-time the position of a tumor. More specifically, the described embodiments can perform image registration based on the acquired ultrasound images and the computed tomography (CT) images used in the radiation treatment plan, so that the position of a tumor can be detected in real-time. Because the radiation treatment room is an environment subject to highly ionizing radiation, the present invention can use a robotic manipulator to remotely actuate an ultrasound probe from a site outside the radiation treatment room.

The embodiments of the present invention can customize a fixture cradle (such as the Alpha cradle commercialized by Smithers Medical Product, Inc.) so as to leave a space for the operation of the robotic manipulator and the placement of the ultrasound probe. In this way, the ultrasound probe does not interfere with the displacement of the robotic manipulator, and the ultrasound probe can cooperate with the robotic manipulator.

In order to integrate the ultrasound image into the radiation treatment planning system, the algorithm currently implemented in the radiation treatment software (such as the Eclipse software commercialized by Varian) can be modified, and a new system structure, inferred target volume and region of interest can be created. After the ultrasound image is reconstructed and covered in the beam's eye view, limitation settings, procedure optimization, dosage calculation, etc. can be conducted. The multiple parameters for generating the dosage measures may include dose volume histograms, isodose distribution, and isosurface dose display. In order to compare the CT reconstructed images and the ultrasound images of the target, an abdomen phantom having multiple dissection structures (for example purchased from CIRS Ltd.) suitable for ultrasound and CT scanning can be used as a simulated radiotherapy target. The abdomen phantom can include a hepatic cyst simulating the radiotherapy target, which can be used for image registration and designing the radiation treatment plan. The beam combination, dose distribution and beam's eye view can be digitally reconstructed from the radiograph, which can be formed from the current results of the radiation treatment plan obtained without the target visualization system, and converted into the system that can monitor the irradiated target in real-time. The present invention describes a system in which an operator in a control room can use ultrasound images to monitor in real-time the irradiated target during a radiation treatment.

Embodiment 1

Robotic Manipulator for Remotely Operating an Ultrasonic Probe

Figure 1:
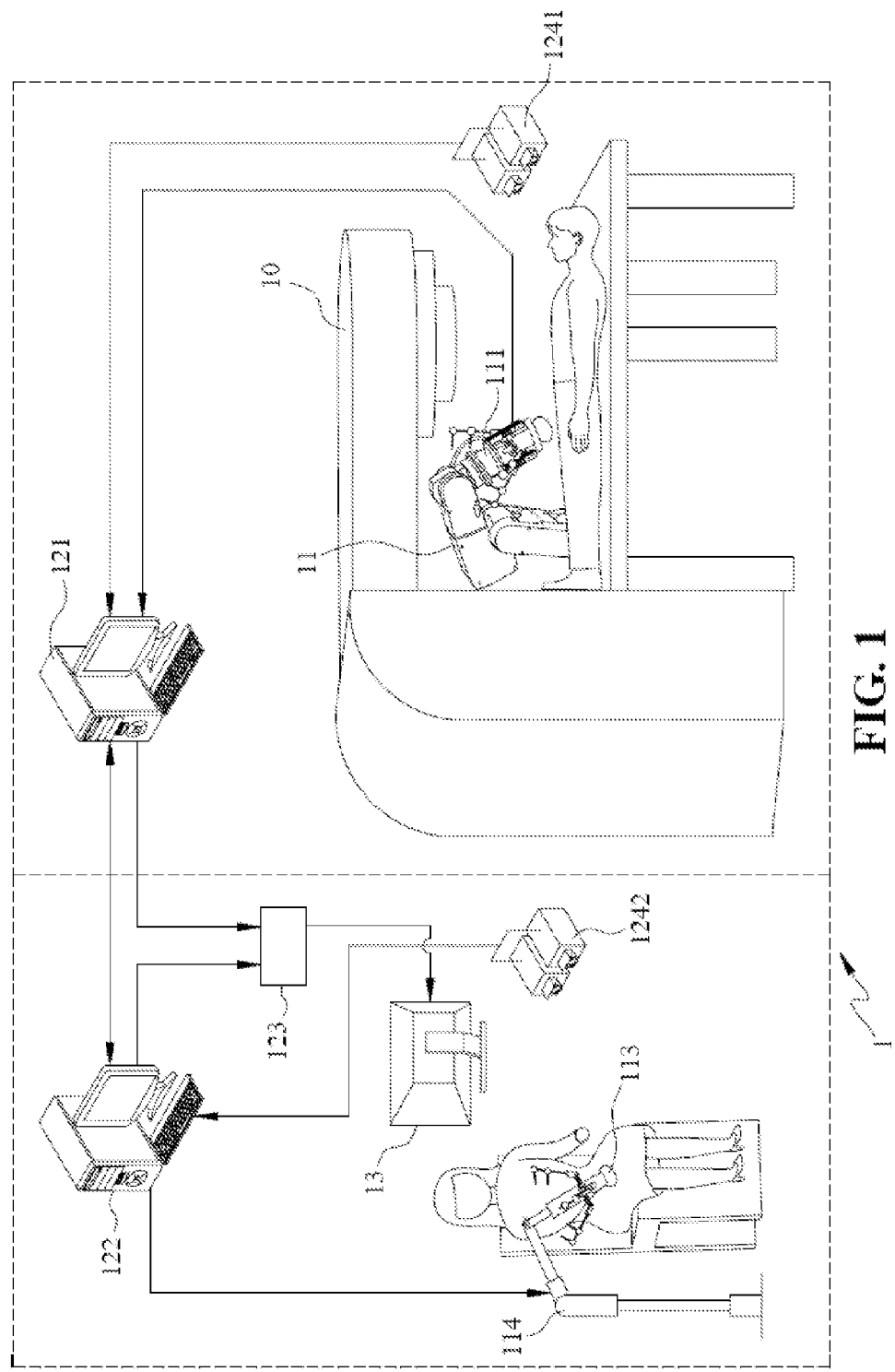
FIG. 1 is a schematic view showing a radiotherapy system adapted to monitor a target location in real time according to the present invention.
Figure 2C:
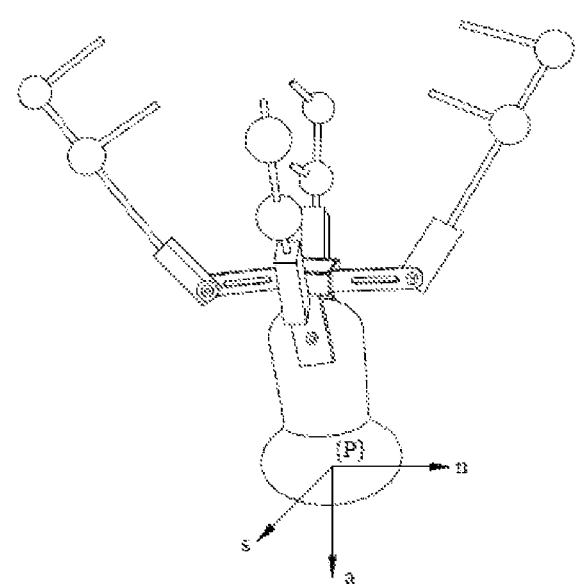
FIG. 2C is a schematic view showing the placement of color balls of different colors and black rods with the handheld probe.

A displacement follower controlling apparatus is needed for the operator to real-time actuate the ultrasonic probe without entering the radiation treatment chamber. As shown in FIG. 1, the radiotherapy system 1 adapted to real-time monitor the position of a target includes an irradiation source 10, and a remote actuating system including a robotic manipulator 11 and a visual servoing and force control system 12. The visual servoing and force control system 12 includes computers 121 and 122, a multiplexer 123, and binocular cameras 1241 and 1242, and a handheld probe 113. The binocular cameras 1241 and 1242 are color digital cameras comprised of charge coupling devices (for example, the model Guppy F-080C manufactured by German company AVT). The robotic manipulator 11 has six degrees of movement (for example the model Mitsubishi RV-1A), which is provided with a six-axis force sensor 111 (for example the sensor sold by the company ATI under the model name Gamma) and an ultrasound probe 112 (as shown in FIGS. 2A-2C). The ultrasound probe 112 can be affixed an end-effector of the robotic manipulator 11. The handheld probe 113 placed in the operating room can be associated with the binocular cameras 1241 and 1242 to issue movement commands. The movement commands can be used to operate the robotic manipulator 11, so that the ultrasound probe 112 can effect the same pose as the handheld probe 113. The position and orientation of inclination of the ultrasound probe 112 relative to the robotic manipulator 11 can be determined based on color balls 1122 and 1132 of different colors and black rods 1121 and 1131 which are respectively disposed on the ultrasound probe 112 and the handheld probe 113. FIG. 2A is a schematic view showing the robotic manipulator 11 provided with the ultrasound probe 112, the color balls 1122 and the black rods 1121, FIG. 2B is a schematic view showing the handheld probe 113 provided with the color balls 1132 and the black rods 1131, and FIG. 2C is a schematic view showing the handheld probe 113 provided with the color balls 1132 of different colors and the black rods 1131. The respective locations of the color balls 1122 of different colors and the black rods 1121 provided on the ultrasound probe 112 can correspond to those of the color balls 1132 and black rods 1131 provided on the handheld probe 113, and their respective orientations are also identical. The camera 1241 can capture an image of the color balls 1122 and black rods 1121 of the ultrasound probe 112 provided on the robotic manipulator 11, and the camera 1242 can capture an image of the color balls 1132 and black rods 1131 provided on the handheld probe 113. The locations of the black rods on the two images can be used as segment features, and the intersections of the black rods (or segment features) can be used as point features that correspond to the color balls in the space reference. The spatial poses of the ultrasound probe 112 and the handheld probe 113 can be determined based on the relative locations of the color balls.

The images containing point and segment features of the ultrasound probe 112 and handheld probe 113 captured by the cameras 1241 and 1242 can be processed by the computers 121 and 122. The data computed by the computers 121 and 122 can be transmitted through the multiplexer 123 to a display device 13 for presentation of control information (such as the position, inclination, and applied force of the robotic manipulator) to an operator. In addition to showing the information of the applied force (force-reflection information) on the display device 13, the force-reflection information detected from six-axis force sensor 111 can be transmitted to a force-reflection robotic manipulator 114 through the computers 121 and 122. Then the force-reflection robotic manipulator 114 makes the handheld probe 113 to perform the force-reflection information, i.e. the handheld probe 113 has two functions: operating the ultrasound probe 112 and performing the force-reflection information. By using the force-reflection robotic manipulator 114, the operator can feel more like operating the ultrasound probe 112 to the human body directly, while the operator operates the handheld probe 113 actually.

The pose of the ultrasound probe 112 (position and orientation) can be transmitted to the visual servoing system in the radiation treatment room for control. First, images containing point and segment features of the handheld probe 113 are captured by the camera 1242 and transmitted to the computer 122 for processing. An instruction then is transmitted through the multiplexer 123 to the computer 121 for processing to actuate the robotic manipulator 11. The camera 1241 then can capture an image containing point and segment features of the end-effector of the robotic manipulator 11, and transmit it to the computer 121 that determines whether the instructed position has been reached. The movement of the ultrasound probe 112 at the end-effector of the robotic manipulator 11 can be thereby controlled according to the displacement instructed by the operator. More specifically, control instructions of combined force and positioning settings can be encoded, such that the ultrasound probe 112 provided on the robotic manipulator 11 can follow the displacement and positioning of the handheld probe 113 held with the operator's hand through visual servoing control. This implementation can be realized through two personal computers equipped with the Intel Core Quad Q6600 2.4 Ghz CPU.

The robotic manipulator 11 has multiple joints. To determine the forward kinematics of the robotic manipulator 11, a coordinate frame may be associated with each of the joints of the robotic manipulator 11, as well as the relationship between the coordinate frames. In particular, the relationship between any pair of coordinate frames can be decomposed into a rotation matrix and a translation vector as shown in FIG. 3A.

Figure 3A:
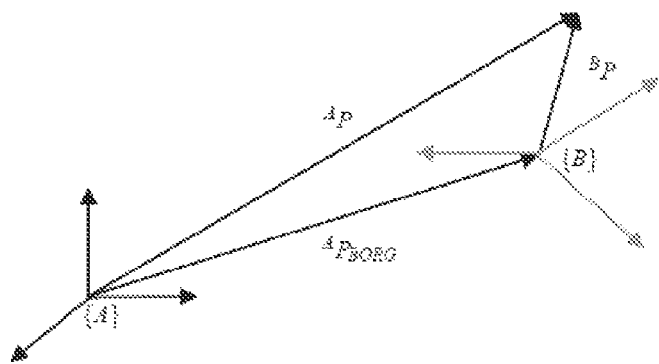
FIG. 3A shows a relationship between any pair of coordinate frames decomposed into a rotation matrix and a translation vector.

In FIG. 3A, the relationship between the coordinate frame {A} and the coordinate frame {B} can be expressed with the following formulae:

$$^A P = {}^A_B R\, ^B P + {}^A P_{BORG}$$

wherein $^A P$ is a vector {P} expressed in the coordinate frame{A}; $^B P$ is the vector {P} expressed in the coordinate frame {B}; $^A_B R$ is a rotation matrix of the coordinate frame {B} relative to the coordinate frame{A}; and $^A P_{BORG}$ is a translation vector of an origin in the coordinate frame {B} relative to the coordinate frame {A}.

The aforementioned relationship can also be expressed as follows:

$$^A \overline{O} = {}^A_B T\, ^B \overline{P}$$

wherein $$^A \overline{P} = \begin{bmatrix} ^A P \\ 1 \end{bmatrix},\, ^B \overline{P} = \begin{bmatrix} ^B P \\ 1 \end{bmatrix},\, ^A_B T = \begin{bmatrix} ^A_B R & ^A P_{BORG} \\ 0 & 1 \end{bmatrix}$$

Figure 3B:
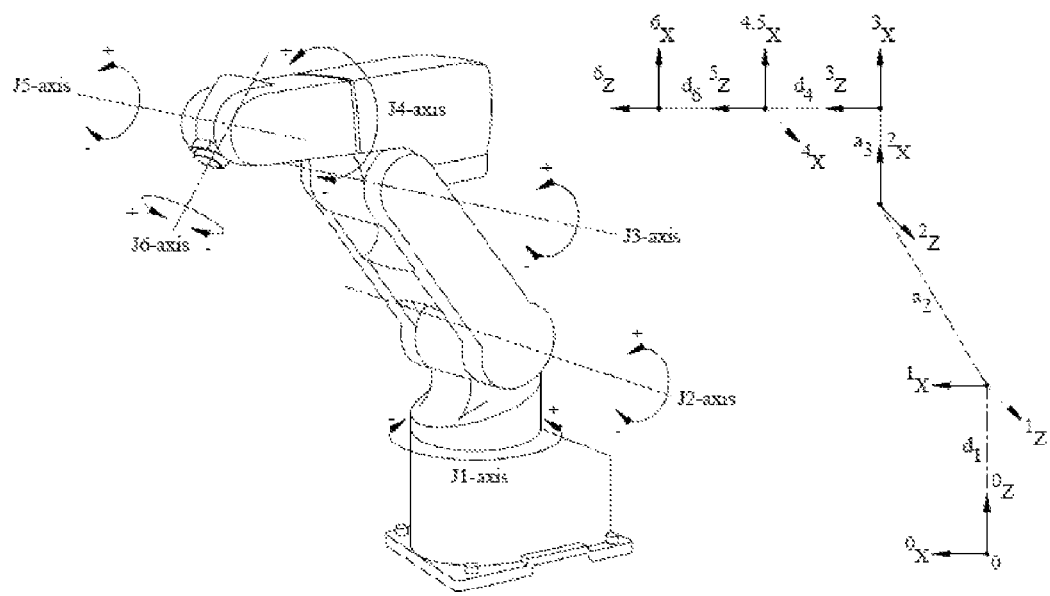
FIG. 3B is a schematic view showing coordinate frames associated with the robotic manipulator.

Accordingly, when each rotary joint of the robotic manipulator is associated with the aforementioned coordinate frame, the relationship between each pair of coordinate frames can be applied to calculate the mapping from a base coordinate frame of the robotic manipulator to each rotary joint, as shown in FIG. 3B. Based on the coordinate frame defined for each joint, a link parameter table D-H can be derived as shown in Table 1:

TABLE 1

| i | αi | ai | θi | di |
|---|-----|-----|-----|-----|
| 1 | -90 | 0   | θ1  | 300 |
| 2 | 0   | 250 | θ2  | 0   |
| 3 | -90 | 90  | θ3  | 0   |
| 4 | 90  | 0   | θ4  | 160 |
| 5 | -90 | 0   | θ5  | 0   |
| 6 | 0   | 0   | θ6  | 72  |

Based on the results derived from the link parameter table, the mapping between the coordinate frame {6} and the base coordinate frame{0} of the robotic manipulator can be expressed with the following formulae:

$$_6^0T = {_1^0T}\,{_2^1T}\,{_3^2T}\,{_4^3T}\,{_5^4T}\,{_6^5T}$$

wherein $$_i^{i-1}T = \begin{bmatrix} \cos\theta_i & -\cos\alpha_i\sin\theta_i & \sin\alpha_i\sin\theta_i & a_i\cos\theta_i \\ \sin\theta_i & \cos\alpha_i\cos\theta_i & -\sin\alpha_i\cos\theta_i & a_i\sin\theta_i \\ 0 & \sin\alpha_i & \cos\alpha_i & d_i \\ 0 & 0 & 0 & 1 \end{bmatrix}$$

Figure 4:
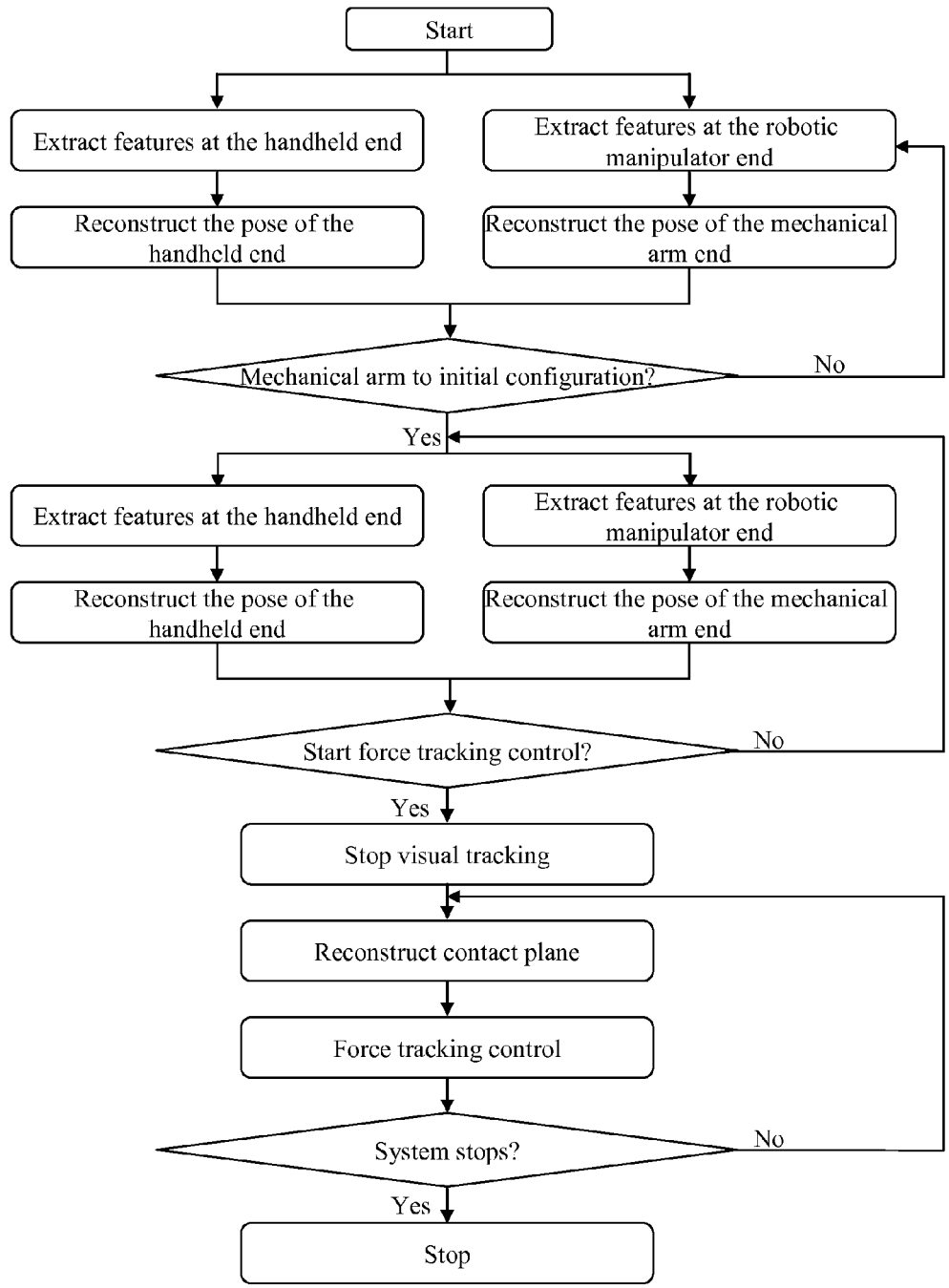
FIG. 4 is a flowchart showing a control method applied by the visual servoing and force control system.

FIG. 4 is a flowchart showing a control method of the visual servoing and force control system 12. When the system is activated, the cameras 1241 and 1242 can respectively capture the image of the ultrasound probe 112 on the robotic manipulator 11 and the image of the handheld probe 113 on the operator's hand in a simultaneous way. The captured images are then processed to define the locations of the segment and point features of the handheld probe 113 and ultrasound probe 112 in accordance with the color balls of different colors and the black rods. Once the locations of the point and segment features are found in the images, the pose of the end-effector can be reconstructed based on the mapped features in the left and right images, and task encoding can be performed. After the task encoding is completed, the encoding results can be substituted into the pose controller. At the same time, the force sensor 111 of the six joints on the robotic manipulator transmits the information of the force measures to a force controller. The control commands of the combined pose and force outputted from the handheld probe 113 then can be considered to apply tracking control on the end-effector of the robotic manipulator 11. While tracking control is performed, the operator can also monitor image and force feedback information on the display device 13. Therefore, while the effector of the robotic manipulator 11 can follow the displacement of the handheld probe 113 in the operator's hand, the six-axis force sensor 111 can also detect a feedback force to determine a force that is applied on the patient. As a result, the application of excessive force can be prevented to avoid uncomfortable feeling from the patient, and a desirable force can be achieved on the surface of the patient's body. This force tracking control can keep the desirable force on the surface of the patient's body to prevent the ultrasound probe from moving out of contact with the patient's body, even when the patient is moving. As the ultrasound probe is continuously maintained in contact with the patient's body surface, desirable image quality can be provided from the ultrasound probe.

Figure 5:
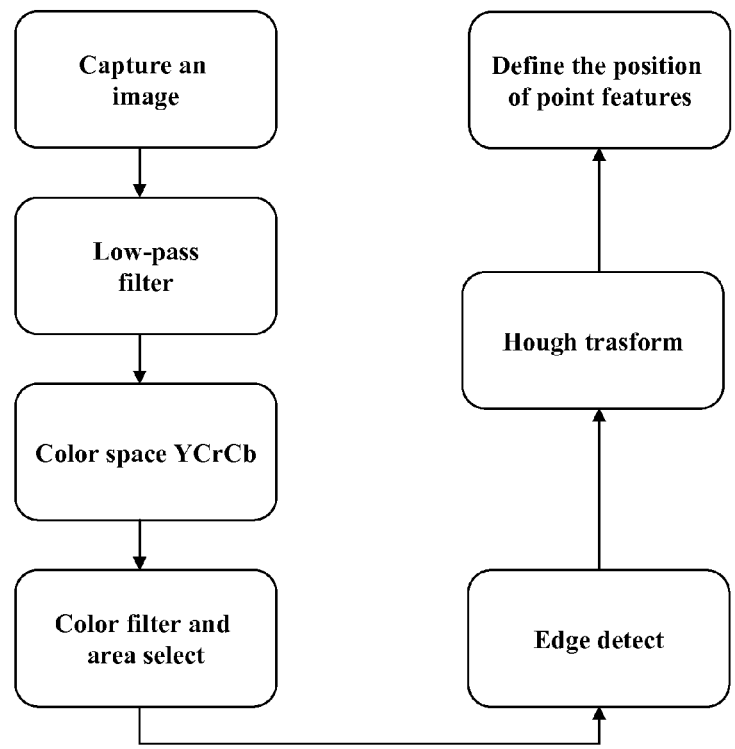
FIG. 5 is a flowchart showing processing steps applied on feature images.

FIG. 5 is a flowchart showing a method of processing images of the point and segment features of the ultrasound probe 112 and handheld probe 113. First, a low-pass filter can be used to remove high-frequency noise. The images captured by the cameras in the RGB color space then are converted into the YCrCb color space for detecting the point and segment features, wherein Y is the luminance, and Cr and Cb are chrominance components that respectively represent differences between the red and blue components in the RGB color space and the luminance Y. In the YCrCb color space, $Y=0.299 \times R+0.587 \times G+0.114 \times B$, $Cr=(R-Y) \times 0.713+128$, and $Cb=(B-Y) \times 0.564+128$. The ranges of the black color that can be defined for the black segment feature include $0<Y<60$, $120<Cr<130$, and $120<Cb<135$. The ranges of the red color that can be defined for the red ball feature include $0<Y<100$, $100<Cr<255$, and $150<Cb<255$. The ranges of the blue color that can be defined for the blue ball feature include $10<Y<140$, $140<Cr<255$, $80<Cb<255$. The ranges of the green color that can be defined for the green ball feature include $0<Y<180$, $0<Cr<130$, $0<Cb<120$. The ranges of the yellow color that can be defined for the yellow ball feature include $100<Y<240$, $120<Cr<150$, and $110<Cb<140$. However, the aforementioned ranges may change according to the brightness of the environment and the aperture of the cameras. Then an edge detecting method, such as the Sobel operator, can be applied to enhance edges of the images. Subsequently, a Hough transform can be applied to retrieve the features from the images. Intersection points then can be derived from the segment features determined from the Hough transform. Because the pose of the segment features on the images may timely change, the sequence of the intersection points on the images may also vary. Accordingly, the ball features of different colors can be used to define the correct locations of the intersection points.

Figure 6:
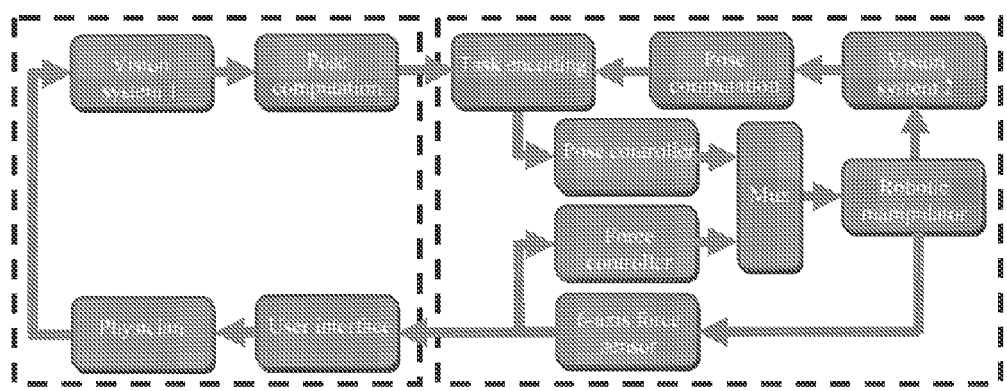
FIG. 6 is a diagram showing the architecture of the visual servoing and force control system.

FIG. 6 is a schematic diagram showing an image servo control system. According to the predetermined geometrical features, a position command r* and an orientation command θ* can be determined from a measure y* of the camera visual system. The mathematical model of the camera visual system can be expressed by the following perspective projection function $G_1$:

$$\begin{bmatrix} r^* \\ \theta^* \end{bmatrix} = G_1(y^*)$$

Likewise, the pose of the ultrasound probe held by the robotic manipulator can be derived from the real-time image measure y applied with the function $G_2$ of the camera visual system as follows:

$$\begin{bmatrix} r \\ \theta \end{bmatrix} = G_2(y)$$

The pose encoded error includes a difference between a current pose and its desired pose, which can be defined as follows:

$$e = \begin{bmatrix} e_r \\ e_\theta \end{bmatrix} = \begin{bmatrix} r - r^* \\ \theta - \theta^* \end{bmatrix}.$$

A contact force f can be directly measured from the force sensor that is kept in desirable contact force $f_d$. A force encoded error $e_f$ can be defined as follows:

$$e_f = f - f_d.$$

Should the point setting be considered in the pose command, the pose encoded error e and a control input u transmitted to the end-effector of the robotic manipulator can be expressed by the following dynamic equation:

$$\dot{e} = \begin{bmatrix} \dot{r} \\ \dot{\theta} \end{bmatrix} = \begin{bmatrix} u_r \\ u_\theta \end{bmatrix} = u$$

wherein $\dot{e}$, $\dot{r}$, $\dot{\theta}$ respectively represent the first time derivatives of e, r and θ.

The following combined force and visual servoing control law can cause the combined encoding error (including the pose encoded error and the force encoded error) to timely converge toward 0, wherein $k_r$ and $k_\theta$ are positive gain coefficients. The convergence of the combined encoding error toward 0 means that the hybrid pose and force control task has been accurately completed.

$$u = -\begin{bmatrix} k_r & 0 \\ 0 & k_\theta \end{bmatrix} e + \begin{bmatrix} u_f \\ 0 \end{bmatrix}$$

wherein $u_f$ is a control law defined as follows:

$$u_f = k_f e_f \hat{n}$$

wherein $k_f$ is a positive gain coefficient, and $\hat{n}$ is a unit vector normal to the contact plane.

The ultrasound probe affixed on the end-effector of the robotic manipulator can be controlled to reach the pose of the probe held by the operator. The pose and the contact force can converge from any initial value. The ultrasound probe affixed with the end-effector of the robotic manipulator can reach the targeted pose in position and orientation within 13 seconds, and the force can reach the targeted value within 11 seconds. More particularly, the pose and force can converge as shown in Table 2. During experiment, the visual servoing control system can effectively reaches a desirable pose.

TABLE 2

|  | Initial value | Target value | Time duration |
|---|---|---|---|
| Position X | 288.108 mm | 443.086 mm | 13 sec |
| Position Y | 52.036 mm | 82.430 mm | 7 sec |
| Position Z | 327.245 mm | 360.730 mm | 8 sec |
| Orientation X | −170.873 deg | −177.859 deg | 9 sec |
| Orientation Y | 25.373 deg | 44.714 deg | 9 sec |
| Orientation Z | −176.95 deg | −177.820 deg | 3 sec |
| Force | 0N | 10.7N | 11 sec |

Embodiment 2

Edge-Based Image Registration

As described in the Embodiment 1, a remotely controlled system can be associated with an ultrasound probe 112 to capture in real-time images of a target under radiation treatment. Moreover, the present invention also provides an edge-based technique of registering CT images and ultrasound images. This technique can register images obtained from the ultrasound probe with CT images from the radiation treatment plan to determine whether the target of the radiation treatment is covered in the beam's eye view. Therefore, the present invention also includes an image registering system in the computer 122.

Figure 7:
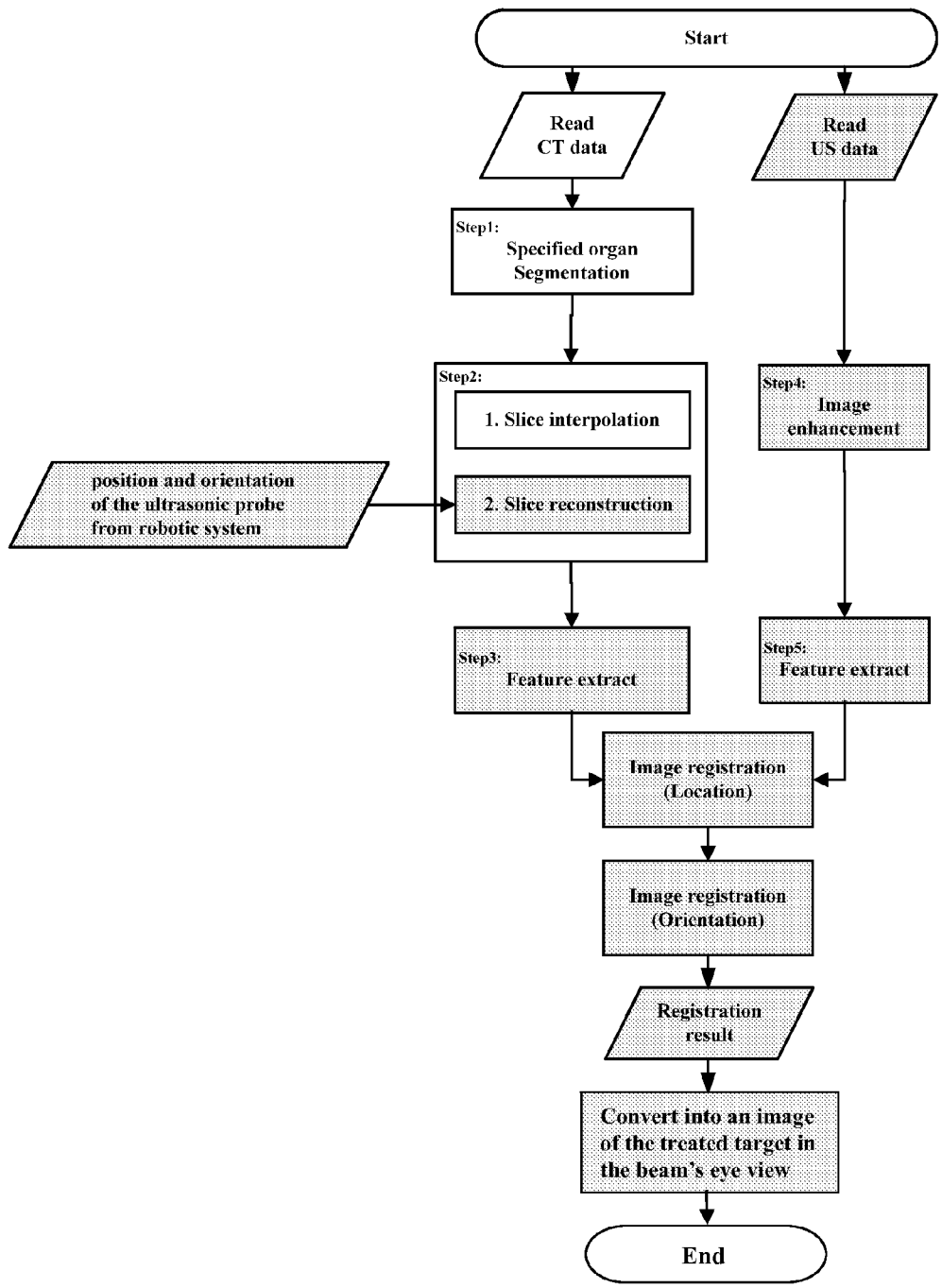
FIG. 7 is a flowchart showing an image registration method according to an embodiment of the present invention.

FIG. 7 is a flowchart of an image registering method according to an embodiment of the present invention. The CT image can be segmented by applying a region growing method, so as to identify an image region of a target organ. An interpolation method then can be applied to derive a 3-dimensional (3D) CT image of the target organ. The image obtained from the ultrasound probe then can be used to select a section at a same orientation as that of the ultrasound probe. Finally, an artificial body manufactured by the company CIRS can be used to undergo testing. With the aforementioned method, registering results can be obtained in a fast and accurate way.

Method steps of processing the CT images are as follows. A region growing method is performed to segment a CT image and obtain a region of a target organ. A 3D image then can be reconstructed from the CT image and information of its axial direction. The 3D CT image then can be affine transformed, and the image of a specific section in the CT image can be reconstructed corresponding to a same section in the ultrasound image. Preprocessing steps including removal of speckle noise, and an algorithm for edge preservation and anisotropic diffusion, then can be applied to extract features.

Because the ultrasound image may have noise and may be subject to deforming distortion, preprocessing steps including an anisotropic diffusion and the application of a median filter of a 5×5 mask can be performed to obtain an image with lower noise. The occurrence of erroneous determination in subsequent edge processing thus can be prevented. The feature extracting step can be similar to the CT image.

Canny edge detection can be applied to extract edge features from the CT image and the ultrasound image. Eventually, a generalized Hough transform can be applied to displace the CT image and the ultrasound image, and register the edge features. A first step in the edge detection method removes noise through a Gaussian filter. A second step uses a Sobel operator to enhance the edges of the image. A third step suppresses non-maximum along a gradient direction, in other words the values of the edge pixels in the gradient direction have to be greater than the values of the adjacent pixels, such that only local maximum are selected as edge points. A fourth step compares the pixel values against two threshold values, namely an upper threshold value T1 and a lower threshold value T2. Any pixel value that is greater than T1 is defined as an edge point, the identified edge points being connected together. Any pixel value that is greater than T2 is also defined as an edge point. A fifth step applies hysteresis thresholding to delete incorrect edge points.

Edge feature registration can use the generalized Hough transform to automatically seek the two following information: 1) a center location of a specific organ, and 2) a refined orientation of the specific organ. First, the edge results found from the CT image and the ultrasound image can be processed through a generalized Hough transform to determine a center offset of the specific organ in the CT image and the ultrasound image. Then a region of interest is expanded from the edges of the specific organ in the CT image, and is registered with the ultrasound image. Next, a generalized Hough transform is applied again to refine the orientation of the specific organ in the CT image and the ultrasound image. Lastly, the ultrasound image which is not in the beam direction is registered with the CT image, and is then converted into an object image of the treated target in the same beam direction of the beam's eye view. In FIG. 7 is also shown a process flow of computing edges of a target object based on the image registration. The process flow includes offline calculation or real-time calculation of the CT image and the ultrasound image. The white region can undergo offline calculation, but the grey region has to undergo real-time calculation. The present embodiment uses a graphic processor unit (GPU) that can work in association with a central processor unit (CPU) to efficiently process ultrasound and CT images in real-time. An example of computer platform can use the compute unified device architecture (CUDA) available from the company Nvidia, and Intel Pentium processors respectively compatible with graphics and central processor units. The GPU can be the GeForce GTX 470, and the CPU can be the Intel® Core™ 2 Duo CPU (2.4 Ghz) with 4 GB of memory.

In one embodiment, the target organ subject to image registration can be a liver. The images can be exemplary scanned from an abdominal phantom. The CT images can include 297 successive images taken along axial planes of the abdominal phantom, the range covering the entire liver. The resolution of the CT images is 512×512 pixels. The scanning interval is 0.5 mm. Therefore, the image size of the abdominal phantom is 512×512×297 pixels. Following Table 3 shows the image format.

TABLE 3

|  | CT image | Ultrasound image |
| --- | --- | --- |
| Gray scale value | 256 | 256 |
| Width (pixel) | 512 | 1024 |
| Length (pixel) | 512 | 768 |
| Scanning interval (mm) | 0.5 |  |
| Pixel spacing (length/width in mm) | 0.5/0.5 | 0.3539/0.3539 |

Figure 8:
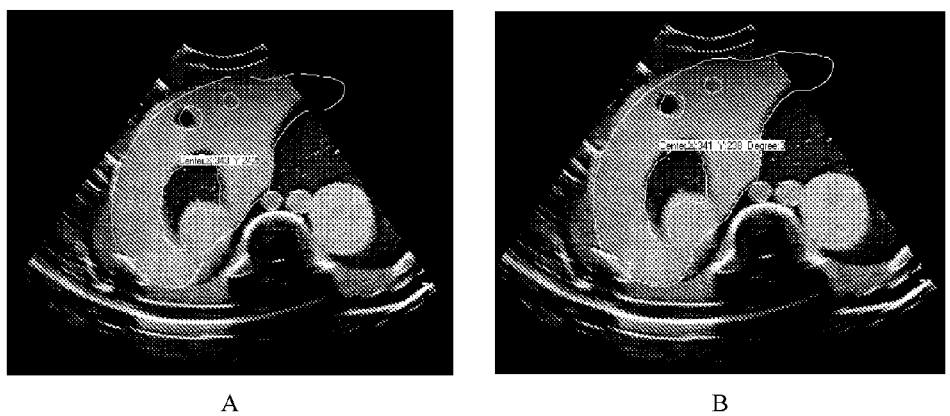
FIG. 8 is a chart showing results of the image registration according to case example 1, wherein A is subject to no rotation, and B is subject to a rotation of 3 degrees.
Figure 9:
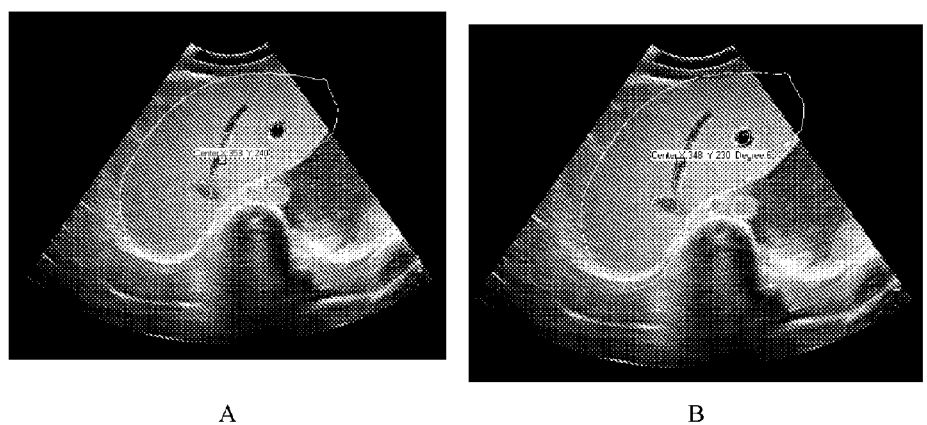
FIG. 9 is chart showing results of the image registration according to case example 2, wherein A is subject to no rotation, and B is subject to a rotation of 6 degrees.

FIGS. 8 and 9 show case test results obtained for cases 1 and 2. Maurer et al (Maurer et al., JComput Assist Tomogr 1996; 20:666-679) proposes two error parameters for analyzing the accuracy of point-based registration methods: 1) a fiducial registration error (FRE) that represents a distance between two corresponding fiducial points of the images after registration, and 2) a target registration error (TRE) that represents a distance between corresponding points other than the fiducial points after registration. Table 4 shows test results of the registration accuracy for different case examples.

TABLE 4

|  | TRE (mm) | FRE (mm) |
| --- | --- | --- |
| Case 1 | 3.3877 | 2.4773 |
| Case 2 | 3.4210 | 5.8776 |

In the two cases, the fiducial registration error and the target registration error are smaller than 10 mm. Table 5 shows the computing time of each step in the implemented method. The real-time computing time is about 235 msec so that the image registration system is available at the actual clinical use.

TABLE 5

|  | Offline computation | Real-time computation (CPU) | Real-time computation (GPU) |
| --- | --- | --- | --- |
| Image segmentation | 180.7 (s) | N/A | N/A |
| Slice interpolation | 8.5 (s) | N/A | N/A |
| Slice reconstruction | N/A | 1.6 (s) | 3 (ms) |
| ultrasound image enhancement | N/A | 1.333 (s) | 22.09 (ms) |
| Feature extraction | N/A | 6 (ms) | 6 (ms) CPU |
| Generalized Hough transform registration | N/A | 11.077 (s) | 204.61 (ms) |
| Total | 189.2 (s) | 14.016 (s) | 235.7 (ms) |

The ultrasound probe 112 can be entirely operated from a remote computer station, which can capture and import/output images in real time. The remote computer station is located outside the radiation treatment room, and can integrate the position servo control computer system operable to control the robotic manipulator in the radiation treatment room to capture images in real time. The control that can be conducted from outside the radiation treatment room can include entirely controlling the functions of the image capture device located in the radiation treatment room, such as switching the ultrasound station from a real-time gray scale imaging mode to a color Doppler imaging mode.

As described in the above Embodiments 1 and 2, the radiotherapy system of the present invention can conduct a radiation treatment and monitor a target location in real time. As radiation treatment is applied, images of the irradiated target (for example tumor) can be simultaneously captured in real time by controlling the robotic manipulator. The ultrasound images obtained from the image registration system then can be registered with the images previously set in the radiation treatment plan to determine whether the irradiated target is in the position set in the radiation treatment plan, and whether the current beam's eye view covers the irradiated target. If the position or orientation of the irradiated target changes due to a displacement of the patient, the parameters can be modified in real time so that the beam's eye view entirely covers the irradiated target, and the peripheral normal tissue can be subjected to a reduced dose of irradiation.

The robotic manipulator can be integrated with a visual servoing and force control system that has multiple degrees of freedom and is equipped with six-axis force sensor. As the robotic manipulator is integrated with a six-axis force sensor and a position servo system, automatic tracking can be achieved to prevent problems caused by displacements of the patient (including body surface, breathing or organ movements). As a result, the image capture device can be locked with the specific region of the patient's body for real-time monitoring. In addition, the operating end can also have force-reflection function, which can improve the touch feeling of the remote operator and also prevent the application of excessive force from the image capture device on the patient's body. Therefore, the safety of the patient can be improved.

The foregoing description is intended to only provide illustrative ways of implementing the present invention, and should not be construed as limitations to the scope of the present invention. While the foregoing is directed to embodiments of the present invention, other and further embodiments of the invention may thus be devised without departing from the basic scope thereof, and the scope thereof is determined by the claims that follow.

What is claimed is:

1. A radiotherapy system capable of monitoring a target position in real time, comprising:
   a radiation source;
   a real-time image capturing device mounted with a robotic manipulator, wherein while radiation is emitted from the radiation source, the real-time image capturing device captures an image of a targeted location in real time;
   a remote actuating system comprised of the robotic manipulator, a remote handheld probe and a visual servoing and force control system, wherein the robotic manipulator has multiple joints with multiple degrees of freedom and is equipped with a multi-axis force sensor, and controlled by the visual servoing and force control system or other position servo control systems to actuate the real-time image capturing device;
   a plurality of color balls and rods configured on the real-time image capturing device and the remote handheld probe, each of the color balls and rods on the real-time image capturing device having a corresponding one on the remote handheld probe, and respective locations and orientations of the color balls and rods on the real-time image capturing device being corresponding and identical to the respective locations and orientations of the color balls and rods on the remote handheld probe;
   a first camera configured to take images of the color balls and rods on the real-time image capturing device, and a second camera configured to take images of the color balls and rods on the remote handheld probe; and
   an image registration system operable to register in real time an image obtained from the real-time image capturing device with a pre-stored image,
   wherein while radiation treatment is conducted, the real-time image capturing device is freely movable on different regions of a patient's body to generate a monitor image, the remote actuating system controlling a position and an orientation of the real-time image capturing device, such that the real-time image capturing device is placed at the targeted location, and is kept in position with a desirable contact force on the targeted location of the patient's body; and
   wherein spatial poses of the real-time image capturing device and the remote handheld probe are determined by the images captured respectively by the first and second cameras and the multiple joints of the robotic manipulator are controlled based on analyzing the spatial poses in combination with contact force detected by the multi-axis force sensor so that the real-time image capturing device is controlled by the remote actuating system to reach a corresponding position and a corresponding angle when the position and the angle of the remote handheld probe are adjusted.

2. The system of claim 1, wherein the radiation source comprises a linear accelerator, a cyclotron, an isotope, or a synchronous accelerator.

3. The system of claim 1, wherein the radiation source is associated with a teletherapy system, or a brachytherapy system.

4. The system of claim 3, wherein the teletherapy system comprises a radiotherapy system using beam's eye view, and the brachytherapy system comprises a radiotherapy system applying image registration.

5. The system of claim 1, wherein the targeted location is a location other than a skull.

6. The system of claim 1, wherein the real-time image capturing device is an ultrasound probe or an image monitoring device held by the robotic manipulator.

7. The system of claim 1, wherein the robotic manipulator has six joints with six degrees of freedom and is equipped with a six-axis force sensor, and the visual servoing and force control system is operable to actuate the robotic manipulator to track and control the position, orientation and contact force of the real-time image capturing device.

8. The system of claim 1, wherein the pre-stored image is a computed tomography image, a positron emission tomography-computed tomography image, or a nuclear magnetic resonance image.

9. The system of claim 1, wherein the image registration system is operable to perform image segmentation, image slice interpolation and slice reconstruction, feature extraction, and image registration.

10. The system of claim 9, wherein the image segmentation processes an image to separate an image region of a treated target.

11. The system of claim 9, wherein the slice reconstruction uses position and orientation information of the real-time image capturing device returned by the visual servoing and force control system to reconstruct an image under the same orientation.

12. The system of claim 9, wherein the feature extraction extracts edge features.

13. The system of claim 9, wherein the image registration system computes a first image obtained from the real-time image capturing device and a pre-stored image, the first image not in a beam direction of a radiation beam of the radiation source is registered with the pre-stored image so that it is converted into an object image of a treated target in beam's eye view of the radiation beam, wherein the real-time image capturing device is an ultrasound probe or an image monitoring device held by the robotic manipulator and the pre-stored image is a computed tomography image, a positron emission tomography-computed tomography image, or a nuclear magnetic resonance image.

14. The system of claim 6, wherein the ultrasound probe is an external 2D probe, an internal probe, a mechanical 3D probe, a freehand 3D probe, a matrix 3D probe, or a real-time 4D probe.

15. The system of claim 6, wherein the ultrasound probe applies real-time gray scale imaging, color and power Doppler imaging, harmonic sonography, sonographic elastography, or contrast enhancement ultrasonography.

16. The system of claim 6, wherein the real-time image capturing device captures images for the image registration system in real-time for assessment by a doctor.

17. The system of claim 6, wherein the real-time image capturing device is entirely controlled by a remote computer station, and is operable to capture and transmit images.

18. The system of claim 1, wherein the other position servo systems comprise magnetic or electronic position servo systems.

19. The system of claim 1, wherein the visual servoing and force control system has a force-reflection function.

* * * * *